US00PP07862P

United States Patent [19]

Jessel, Jr.

[11] Patent Number: Plant 7,862

[45] Date of Patent: May 5, 1992

[54] CARNATION PLANT NAMED 'CFPC CHANÓN'

[75] Inventor: Walter H. Jessel, Jr., Salinas, Calif.

[73] Assignee: California Florida Plant Co., L.P., Salinas, Calif.

[21] Appl. No.: 580,255

[22] Filed: Sep. 10, 1990

[51] Int. Cl.[5] ..... A01H 5/00

[52] U.S. Cl. ..... Plt./71

[58] Field of Search ..... Plt./70, 71, 72

[56] References Cited

U.S. PATENT DOCUMENTS

P.P. 398 5/1940 Okada ..... Plt. 71

P.P. 5,515 7/1985 Barberet et al. ..... Plt. 71

*Primary Examiner*—Howard J. Locker

*Attorney, Agent, or Firm*—Christie, Parker & Hale

[57] ABSTRACT

A new and unusual carnation of substantially true pink coloration.

1 Drawing Sheet

BACKGROUND OF THE INVENTION

Carnation varieties producing flowers of many different colors are well known. However, it is desirable to provide a new standard variety of carnation producing flowers having substantially true pink coloration which is resistant to excessive fading.

SUMMARY OF THE INVENTION

The present invention relates to a new and distinct variety of carnation plant which was originated by me in a controlled breeding program by my crossing as seed parent, the variety known as 'Vanya' (varietal denomination 'Londapo') (U.S. Plant Pat. No. 5,515) and as pollen parent, a numbered but unnamed and unpatented seedling of my creation. The varietal denomination of this new carnation is 'CFPC Chanón'.

Among the novel characteristics possessed by the new variety which distinguishes it from its parents and all other varieties of which I am aware is the unusual true pink flower coloring in a standard. Flowers of the new variety are resistant to excessive fading and have strong stems.

Asexual reproduction by propagation by side shoot cuttings of the new variety as performed in Fremont and Salinas, Calif., shows that the foregoing and other distinguishing characteristics come true to form and are established and transmitted through succeeding propagations.

BRIEF DESCRIPTION OF THE ILLUSTRATION

The accompanying illustration shows typical specimens of the vegetative growth and flowers of the new variety in different stages of development (tight bud, partially opened bud and full bloom), depicted in color as nearly true as it is reasonably possible to make the same in a color illustration of this character.

DESCRIPTION OF THE NEW VARIETY

The new variety, 'CFPC Chanón', produces flowers which have a strong calyx with very little splitting. Therefore, taping or banding is not necessary. The new variety produces flowers of unusually pure pink color and of high grade with a high proportion of "fancy" cuts. The flowers hold their color well, have good vase-life and are borne on strong stems. The foliage is long and narrow and curled at the base. 'CFPC Chanón' is especially suitable for commercial cut flower production.

The following is a detailed description of my new variety, with color terminology in accordance with the Royal Horticultural Society Colour Chart (R.H.S.C.C.). The terminology used in the color description herein refers to plate numbers in the aforementioned color chart. Color designations and color descriptions may deviate slightly from the stated values from flowering-to-flowering but the deviations will be within the range expected from varying environmental, seasonal and cultural conditions.

The information provided herein is based on observations of plants grown inside commercial greenhouses at Fremont, Calif. The height of plant and flower and foliage size are established as an average using standard commercial cultrual practices.

Name: CFPC Chanón.

Classification:

*Botanical.*—*Dianthus caryophyllus.*

*Commercial.*—Carnation, standard disbud type.

Parentage:

*Female parent.*—'Vanya'.

*Male parent.*—Unnamed seedling (No. 00167).

Plant:

*Height.*—About 42 inches.

*Growing habit.*—Herbaceous, semi-upright.

*Blooming habit.*—Terminal as a disbud.

*Blooming season.*—Year round.

*Rooting time.*—About 20 days.

*Mutation prone.*—No.

*Disease resistance.*—Unknown.

*Temperature tolerance.*—Typical for carnation.

Foliage:

*Color.*—Upper side: Near to 136A. Lower side: Same as upper side. This is unusual as the reverse is usually lighter.

*Size.*—About 6¾ inches long, about ½-inch wide at base of plant.

*Quantity.*—Numerous.

*Shape.*—Lanceolate.

*Texture.*—Smooth.

*Ribs.*—Central keel.

*Arrangement.*—Bi-lateral along stem.

*Stem.*—Color: Green.

Bud:

*Shape.*—Oval.
*Color.*—Green.
*Length.*—About 1 to $1\frac{1}{4}$ inches.
*Diameter.*—About $\frac{3}{8}$ to $\frac{1}{2}$ inch.

Calyx:
*Number of lobes (sepals).*—About 5.
*Length.*—About $1\frac{1}{4}$ inches.
*Width.*—About $\frac{1}{2}$-inch.
*Color.*—Outside — near to 134A. Inside — near to 130D.

Bloom:
*Shape.*—Round, serrated at petal edge.
*Size.*—Diameter average: About $3\frac{1}{2}$ inches. Depth average: About $2\frac{1}{2}$ inches.
*Borne.*—Terminal as disbudded.
*Color.*—General tonality: True pink, from near 49C to D to near 50D.
*Permanence.*—Yes.
*Keeping habit.*—Good.
*Fragrance.*—Very slight.

Petals:
*Number.*—About 40-45.

*Outer petals.*—Length: About $1\frac{7}{8}$ inches. Width: About $1\frac{3}{8}$ inches.
*Texture.*—Smooth.
*Form.*—Fan shaped.

Reproductive organs: Not visible in this variety.
*Stamen.*—Number: About 13. Arrangement: Around the ovary.
*Anthers.*—Number: About 13. Length: About 1/5-inch. Color: Near to 164B.
*Filaments.*—Length: About $\frac{5}{8}$ to 1-inch. Color: Near to 155D.
*Pistil.*—Number: About 3. Length: About $1\frac{1}{2}$ inches. Color: Style — near to 155B.
*Stigma.*—Number: About 3. Color: Near to 56D.
*Fertility.*—Male: Very poor. Female: Average.
*Ovary.*—Shape: Conical, ribbed. Color: Base — greenish white. Body — Greenish yellow. Apex — tan.

I claim:

1. A new and distinct variety of carnation plant, substantially as shown and described, characterized particularly by flowers of attractive pink coloration.

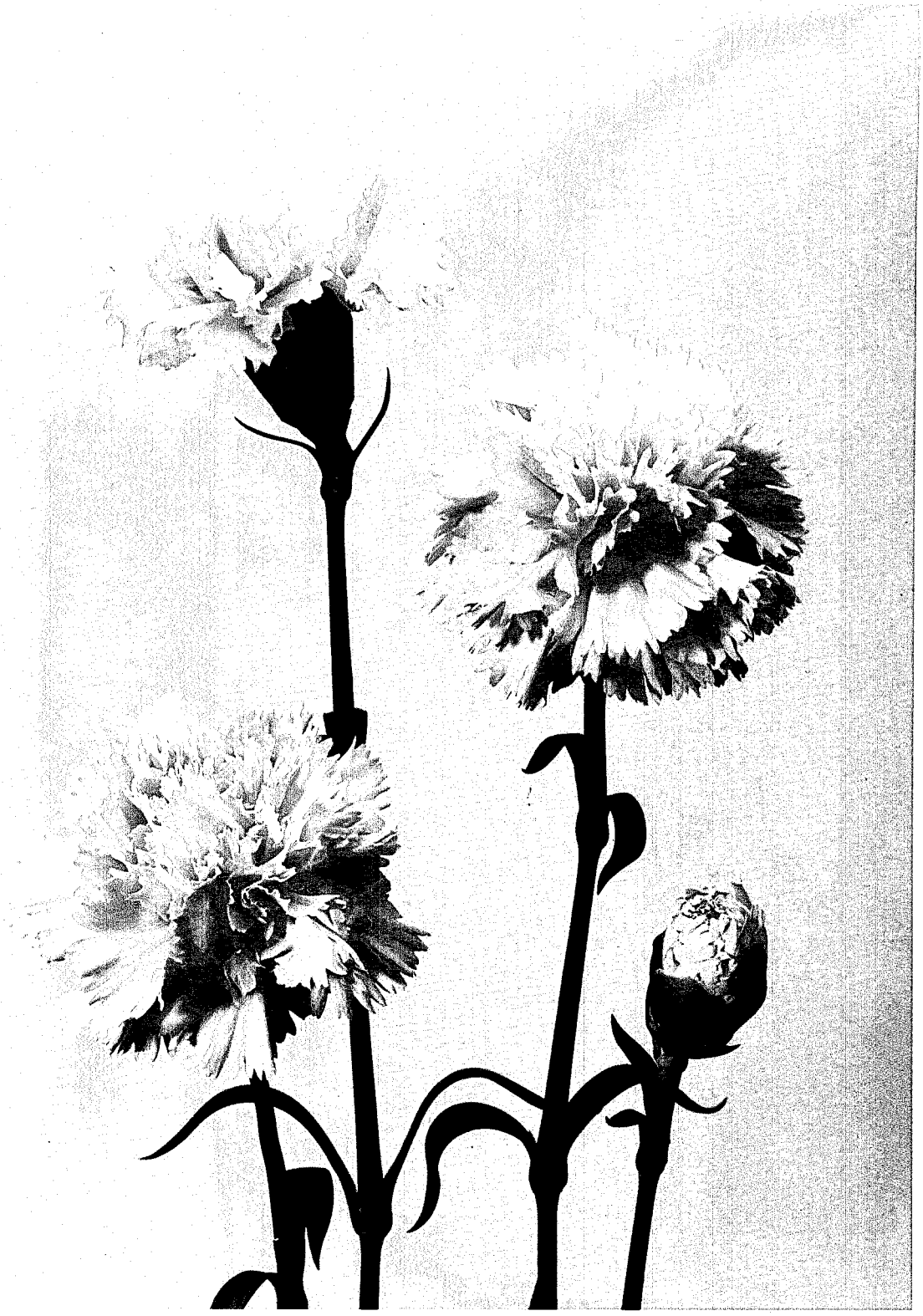

* * * * *